United States Patent [19]

Pialet et al.

[11] Patent Number: 4,784,782
[45] Date of Patent: Nov. 15, 1988

[54] HETEROCYCLIC COMPOUNDS USEFUL AS ADDITIVES FOR LUBRICANT AND FUEL COMPOSITIONS

[75] Inventors: Joseph W. Pialet, Euclid; Paul E. Adams, Willoughby, both of Ohio

[73] Assignee: The Lubrizol Corporation, Wickliffe, Ohio

[21] Appl. No.: 845,204

[22] Filed: Mar. 27, 1986

[51] Int. Cl.$^4$ .............. C10M 133/00; C10C 1/14
[52] U.S. Cl. .............. 252/47.5; 252/51.5 R; 252/49.9; 252/47; 252/77; 252/51.5 A; 44/63; 44/71; 44/76; 540/364; 540/485; 540/526; 540/527; 540/529; 546/286; 546/288; 546/291; 546/293; 546/298; 548/567; 549/61; 549/62; 549/63; 549/64; 558/73
[58] Field of Search .............. 252/47, 47.5, 51.5 R, 252/49.9; 44/76, 63, 71; 540/364, 485, 526, 527, 529; 546/286, 288, 291, 293, 298; 548/567; 549/61, 62, 63, 64; 558/73

[56] References Cited

U.S. PATENT DOCUMENTS

| | | | |
|---|---|---|---|
| 2,704,761 | 3/1955 | D'Amico | 252/47.5 |
| 3,901,815 | 8/1975 | Reale, Jr. | 252/47.5 |
| 3,971,792 | 7/1976 | Zondler et al. | 260/293.52 |
| 3,981,878 | 9/1976 | Curran | 260/293.73 |
| 3,984,336 | 10/1976 | Cier et al. | 252/47.5 |
| 4,009,274 | 2/1977 | Curran | 424/263 |
| 4,038,197 | 7/1977 | Caspari | 252/47.5 |
| 4,178,253 | 12/1979 | Lee et al. | 252/47.5 |
| 4,189,587 | 2/1980 | Holt et al. | 252/47.5 |
| 4,194,982 | 3/1980 | Chou | 252/47.5 |
| 4,289,635 | 9/1981 | Schroeck | 252/32.7 |
| 4,326,972 | 4/1982 | Chamberlin, III | 252/33.3 |
| 4,432,847 | 2/1984 | Fields | 252/47.5 |

FOREIGN PATENT DOCUMENTS 1122110  11/1966  United Kingdom .

Primary Examiner—William R. Dixon, Jr.
Assistant Examiner—Cynthia A. Prezlock
Attorney, Agent, or Firm—Denis A. Polyn; Forrest L. Collins; Karl Bozicevic

[57] ABSTRACT

Various heterocyclic compounds have been discovered that impart improved fuel economy and friction modification to lubricant and fuel compositions. These heterocyclic compounds of the invention preferably contain nitrogen and may be further reacted with hydrocarbyl carboxylic acid acylating reactants or hydrocarbyl phenolic reactants to give higher molecular materials. These higher molecular weight materials have higher oil-solubility and impart dispersancy properties to lubricant and fuel compositions.

17 Claims, No Drawings

HETEROCYCLIC COMPOUNDS USEFUL AS ADDITIVES FOR LUBRICANT AND FUEL COMPOSITIONS

BACKGROUND OF THE INVENTION

1. Field of the Invention

This invention relates generally to various heterocyclic compounds, preferably nitrogen containing heterocyclic compounds, useful as additives for lubricant and fuel compositions. The additives of the present invention when formulated with a lubricant or fuel composition provide improved fuel economy and friction modification in an internal combustion engine. The heterocyclic compound additives of the present invention may be reacted with a hydrocarbyl carboxylic acylating reactant or a hydrocarbyl phenolic reactant to form a higher molecular weight product to impart greater solubility and dispersancy in various lubricant and fuel compositions as well as providing improved fuel economy.

2. State of the Art

Reducing fuel consumption and improving the operation of internal combustion engines has been an objective in the industry since the early 1970's. Since that time, a number of additives have been developed in an attempt to achieve this objective.

For example, U.S. Pat. No. 4,326,972 discloses a lubricating oil formulated with a specific sulfurized composition and a basic alkali metal sulfonate to provide improved fuel economy of internal combustion engines.

U.S. Pat. No. 4,289,635 discloses various molybdenum compounds of phosphorus acids which are useful for formulating with lubricating compositions for improved fuel economy of internal combustion engines.

Heterocyclic amino, specifically amino piperidine compounds, have been disclosed in the patent literature. U.S. Pat. No. 3,971,792 discloses a process for the manufacture of 4-amino-3-aminomethyl piperidine which are disclosed as being useful as curing agents for epoxide resins.

Great Britain Pat. No. 1,122,110 discloses 4-imino-3-cyano piperidines wherein the process for preparing these compounds is disclosed.

None of the foregoing disclosures teach the heterocyclic compounds of the present invention useful for providing friction modification and improved fuel economy in lubricant and fuel compositions.

SUMMARY OF THE INVENTION

In accordance with the present invention, various heterocyclic compounds which are useful in lubricant and fuel compositions have been discovered.

Further, in accordance with the invention, the heterocyclic compounds of the present invention may be further reacted with a hydrocarbyl carboxylic acid acylating agent or a hydrocarbyl phenolic reactant to form higher molecular weight products exhibiting improved oil solubility and imparting dispersancy properties to the particular lubricant or fuel composition.

Still further, in accordance with the present invention, it has been found that the heterocyclic compounds of the invention may be used alone as additives for lubricant and fuel compositions or may be further reacted with, for example, hydrocarbyl carboxylic acylating agent to give a higher molecular weight additive product which is formulated with the particular lubricant or fuel composition.

Still further, in accordance with the invention, various lubricant and fuel compositions, including crankcase oils and the like, comprising the various heterocyclic amine compounds or the heterocyclic amine compounds which have been further reacted with a hydrocarbyl carboxylic acid acylating agent or hydrocarbyl phenolic reactant are contemplated and are within the scope of the invention.

These and other aspects of the invention will become clear to those skilled in the art upon the reading and understanding of the specification.

DETAILED DESCRIPTION OF THE INVENTION

The class of heterocyclic compound additives of the present invention may be illustrated by the following formula:

wherein Z is S, NR,

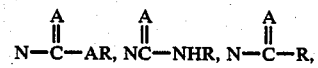

PR or PRA, wherein A is O or S and R is H, alkyl, alkenyl, hydrocarbyl acyl, hydrocarbyl phenolate or $-(CH_2)_mQ$, where m is 1 to about 12, and Q is O-alkyl or N-alkyl, X is independently H, COOH, $NH_2$, $CONH_2$, $NHNH_2$, OR, COR, NHR, OH, SH, or CN wherein R is the same as defined above; p is 0 to 2; e is 0 to 2 wherein e+p is 2 to about 4; T is $NH_2$, NHR wherein R is the same as defined above, SH, OH or their tautomers, hydrocarbyl acyl or hydrocarbyl phenolate; and Y is CN,

$CO_2H$ or $CH_2NH_2$ wherein A is the same as defined above.

As used herein, the terms "hydrocarbyl" or "hydrocarbon-based" denote a radical having a carbon atoms directly attached to the remainder of the molecule and having predominantly hydrocarbon character within the context of this invention. Such radicals include the following:

(1) Hydrocarbon radicals; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, any two indicated substituents may together form an alicyclic radical). Such radicals are known to those skilled in the art.

(2) Substituted hydrocarbon radicals; that is, radicals containing non-hydrocarbon substituents which, in the context of this invention, do not alter the predominantly hydrocarbon character of the radical. Those skilled in the art will be aware of suitable substituents.

(3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbyl radical.

Terms such as "alkyl-based radical", "aryl-based radical" and the like have meaning analogous to the above with respect to alkyl and aryl radicals and the like.

The radicals are usually hydrocarbon and especially lower hydrocarbon, the word "lower" denoting radicals containing up to seven carbon atoms. They are preferably lower alkyl or aryl radicals, most often alkyl.

The heterocyclic compounds of the present invention may be prepared by known processes in the art. For example, these compounds may be prepared from such reactants as dicyanoethylamine, dicyanoethylsulfide or dicyanoethylphosphine. Obviously, the size of the ring is dependent upon the length of the alkylene chain of the reactant. Also, other products within the scope of the present invention may be prepared from such reactants as acetamidoacetone reacted with either a dinitrile reactant or a nitrile ester containing material. The preparation of these materials is described in U.K. Pat. No. 1,122,110; *Org. Synth.*, Volume V, Page 27; *Synthesis*, (1976), Page 51; *Synthesis*, (1974), Page 837; J.C.S., (1962), Page 4664; *J.A.C.S.* 81, 1103; ibid. 82, 4437. The teachings of the foregoing disclosures are incorporated herein by reference for the preparation of the various heterocyclic compounds disclosed therein.

As described in the above references, these reactions are generally conducted in the presence of a base catalyst and refluxed in a solvent to produce the desired heterocyclic compound. The particular base compound reactants, e.g., heterocyclic compounds, of the present invention are defined by the general formula:

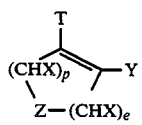
(II)

wherein Z is S, NR',

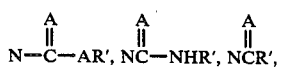

PR' or PR'A where A is O or S and R' is H, alkyl or alkenyl; p is 0 to 2; e is 0 to 2 wherein e+p is 2 to about 4; X is independently H, COOH, NH$_2$, CONH$_2$, NHNH$_2$, OR', COR', NHR', OH, SH or CN, where R' is the same as defined above wherein T is NH$_2$, NHR' where R' is the same as defined hereinabove, SH, OH or their tautomers; and Y is CN, CO$_2$H,

or CH$_2$NH$_2$ wherein A is the same as defined hereinabove.

A preferred group of compounds, for the purposes of the present invention as defined by formula II above, include the compounds where X is H, Z is NR, T is NH$_2$, e is 1 and p is 2. A most preferred group of compounds include the preferred compounds and where Y is CN or CH$_2$NH$_2$.

The above cyclic reaction products (Formula II) are useful as fuel economy additives, detergents, antioxidants, rust inhibitors and antiwear agents. These products (Formula II) may also be further reacted with other reactants/reagents to include substituents which give greater oil solubility, dispersancy and further impart greater VI (viscosity index) improvement to base stock oils. For the purposes of this invention, a substance is considered to substantially improve the viscosity properties of a composition if its incorporation in the composition in operative amounts causes an increase in its viscosity index (as determined by ASTM procedure D2270) of at least 6 units.

In general, materials which may be used to further react with the above described heterocyclic compounds (Formula II) are reagents or reactants which are described in the patent and technical literature.

Among the reactant materials that may be utilized for the purposes of the present invention to further react with the above-described coupled polyamine products to form a higher molecular weight material, there may be first mentioned various hydrocarbyl carboxylic acid acylating reagents. The carboxylic acids useful in this invention include aliphatic, cycloaliphatic, and -aromatic mono- and polybasic carboxylic acids such as the naphthenic acids, alkyl- or alkenyl-substituted cyclopentanoic acids, alkyl- or alkenyl-substituted cyclohexanoic acids, alkyl- or alkenyl-substituted aromatic carboxylic acids. The aliphatic acids generally contain at least eight carbon atoms and preferably at least twelve carbon atoms. Usually, they have no more than about 400 carbon atoms. Generally, if the aliphatic carbon chain is branched, the acids are more oil-soluble for any given carbon atoms content. The cycloaliphatic and aliphatic carboxylic acids can be saturated or unsaturated. Specific examples include 2-ethylhexanoic acid, -linolenic acid, propylene-tetramer-substituted maleic acid, behenic acid, isostearic acid, pelargonic acid, capric acid, palmitoleic acid, linoleic acid, lauric acid, oleic acid, ricinoleic acid, undecyclic acid, dioctylcyclopentane carboxylic acid, myristic acid dilauryldecahydronaphthalene carboxylic acid, stearyloctahydroindene carboxylic acid, palmitic acid, commercially available mixtures of two or more carboxylic acids such as tall oil acids, rosein acids and the like.

A preferred group of oil-soluble carboxylic acids useful in preparing the products used in the present invention are the oil-soluble aromatic carboxylic acids. These acids are represented by the general formula:

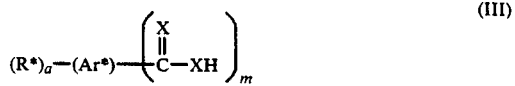
(III)

where R* is an aliphatic hydrocarbon-based group of at least four carbon atoms, and no more than about 400 aliphatic carbon atoms, a is an integer of from one to four, Ar* is a polyvalent aromatic hydrocarbon nucleus of up to about 14 carbon atoms, each X is independently a sulfur or oxygen atoms, and m is an integer of from one to four with the proviso that R* and a are such that there is an average of at least 8 aliphatic carbon atoms provided by the R* groups for each acid molecule represented by Formula (V). Examples of aromatic nuclei represented by the variable Ar* are the polyvalent aromatic radicals derived from benzene, naphthalene, anthracene, phenanthrene, indene, fluorene, biphenyl, and the like. Generally, the radical represented by Ar* will be a polyvalent nucleus derived from benzene or naphthalene such as phenylenes and naphthylene, e.g., methylphenylenes, ethoxyphenylenes, nitrophenylenes, isopropylphenylenes, hydroxyphenylenes, mercaptophenylenes, N,N-diethylaminophenylenes, chlorophenylenes, dipropoxynaphthylenes, triethylnaphthylenes, and similar tri-, tetra-, penta-valent nuclei thereof, etc.

The R* groups are usually purely hydrocarbyl groups, preferably groups such as alkyl or alkenyl radicals. However, the R* groups can contain small number substituents such as phenyl, cycloalkyl (e.g., cyclohexyl, cyclopentyl, etc.) and non-hydrocarbon groups such as nitro, amino, halo (e.g., chloro, bromo, etc.), lower alkoxy, lower alkyl mercapto, oxo substituents (i.e., =O), thio groups (i.e., =S), interrupting groups such as —NH—, —O—, —S— and the like provided the essentially hydrocarbon character of the R* group is retained. The hydrocarbon character is retained for purposes of this invention so long as any non-carbon atoms present in the R* groups do not account for more than about 10% of the total weight of the R* groups.

Examples of R* groups include butyl, isobutyl, pentyl, octyl, nonyl, dodecyl, docosyl, tetracontyl, 5-chlorohexyl, 4-ethyoxypentyl, 4-hexenyl, 3-cyclohexyloctyl, 4-(p-chloro-phenyl)-octyl, 2,3,5-trimethylheptyl, 4-ethyl-5-methyloctyl, and substituents derived from polymerized olefins such as polychloroprenes, polyethylenes, polypropylenes, polyisobutylenes, ethylene-propylene copolymers, chlorinated olefin polymers, oxidized ethylene-propylene copolymers and the like. Likewise, the group Ar* may contain non-hydrocarbon substituents, for example, such diverse substituents as lower alkoxy, lower alkyl mercapto, nitro, halo, alkyl or alkenyl groups of less than four carbon atoms, hydroxy, mercapto and the like.

A group of particularly useful carboxylic acids are those of the formula:

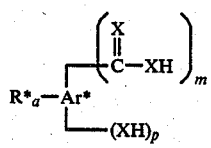

(IV)

where R*, X, Ar*, m and a are defined in Formula (III) and p is an integer of 1 to 4, usually 1 or 2. Within this group, an especially preferred class of oil-soluble carboxylic acids are those of the formula:

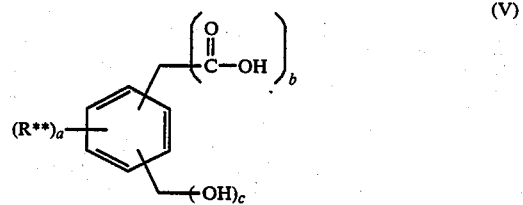

(V)

where R is an aliphatic hydrocarbon group containing at least 4 to about 400 carbon atoms, a is an integer of from 1 to 3, b is 1 or 2, c is zero, 1, or 2 and preferably 1 with the proviso that R and a are such that the acid molecules contain at least an average of about twelve aliphatic carbon atoms in the aliphatic hydrocarbon substituents per acid molecule. And within this latter group of oil-soluble carboxylic acids, the aliphatic-hydrocarbon substituted salicylic acids wherein each aliphatic hydrocarbon substituent contains an average of at least about sixteen carbon atoms per substituent and one to three substituents per molecule are particularly useful. Salts prepared from such salicylic acids wherein the aliphatic hydrocarbon substituents are derived from polymerized olefins, particularly polymerized lower 1-mono-olefins such as polyethylene, polypropylene, polyisobutylene, ethylene-propylene copolymers and the like and having average carbon contents of about 30 to about 400 carbon atoms.

The carboxylic acids corresponding to Formula (III)-(V) above are well known or can be prepared according to procedures known in the art. Carboxylic acids of the type illustrated by the above formula and processes for preparing their neutral and basic metal salts are well known and disclosed, for example, in such U.S. Pat. Nos. as 2,197,832; 2,197,835; 2,252,662; 2,252,664; 2,174,092; 3,410,798 and 3,595,791.

Another type of carboxylate reactant used in this invention is alkenyl succinic acid or derivatives thereof illustrated by the general formula:

(VI)

wherein R* is as defined above in Formula (III). Such reactants and means for making them are set forth in U.S. Pat. Nos. 3,271,130; 3,567,637 and 3,632,510, which are hereby incorporated by reference in this regard.

Preferably, the above described alkenyl substituted succinic acid or derivative thereof consists of substituent groups and succinic groups wherein the substituent groups are derived from polyalkylene, said polyalkylene being characterized by a $\overline{M}n$ value of 100 to about 10,000 and a $\overline{M}w/\overline{M}n$ value of 1.0 to about 4.0. Also, in a preferred embodiment, the substituent group contains from about 8 to about 200 carbon atoms.

Phenolic reactants are also useful for preparing compositions within the scope of this invention and are well known to those skilled in the art. The phenols from which these reactants are formed are of the general formula:

(VII)

wherein R*, n, Ar*, X and m have the same meaning and preferences as described hereinabove with reference to Formula (III). The same examples described with respect to Formula (III) also apply.

A commonly available class of phenolic reactants are those made from phenols of the general formula:

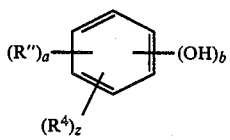

(VIII)

wherein a is an integer of 1–3, b is 1 or 2, z is 0 or 1, R″ is a substantially saturated hydrocarbon-based substituent having an average of from 30 to about 400 aliphatic carbon atoms and $R^4$ is selected from the group consisting of lower alkyl, lower alkoxyl, nitro and halo groups.

Other phenolic reactants that are useful are those that are made from phenols that have been linked through alkylene (e.g., methylene) bridges. These are made by reacting single or multi-ring phenols with aldehydes or ketones, typically, in the presence of an acid or basic catalyst. Such linked phenates as well as sulfurized phenates are described in detail in U.S. Pat. No. 3,350,038; particularly columns 6–8 thereof, which is hereby incorporated by reference for its disclosures in this regard.

Naturally, mixtures of two or more reactants of the hereinabove described carboxylic acids and phenols can be used in the compositions of this invention, including mixtures of two or more of any of these.

The above-described reaction products form additive/dispersant materials described by the general formula (I) wherein R or T is hydrocarbyl acyl or hydrocarbyl phenolate.

The foregoing additives/dispersants are generally prepared by the catalyzed (usually acid catalyzed) reaction of at least one of the heterocyclic amines (e.g., as defined in Formula II) of the present invention with at least one of the reactive materials described hereinabove at an elevated temperature.

In a preferred embodiment of the invention, the reactants are heated to a temperature of from about 80° C. to the decomposition temperature of the mixture to effect acylation or condensation reaction. In a most preferred embodiment, the heating is conducted at a temperature of from about 120° C. to about 175° C. to effect acylation or reaction.

Furthermore, it is preferred, but not critical for the purposes of the invention, that about 0.25 to about 2.0 equivalents of the heterocyclic compound (II) is reacted with each equivalent of the hydrocarbyl carboxylic acid or derivative thereof and/or hydrocarbyl phenolic reactant. Most preferably, about 0.4 to about 0.8 equivalents of the heterocyclic compound (II) are reacted with each equivalent of the hydrocarbyl carboxylic acid or derivatives thereof and/or the hydrocarbyl phenolic reactant.

The following examples are provided to illustrate various specific compounds within the scope of the present invention. It is emphasized that these examples are provided for illustrative purposes only and are not to serve as a limitation on the scope of the invention where such scope is set out solely in the claims.

EXAMPLE I

A substituted succinic anhydride (1314 grams, 3 moles), 4-imino-3-cyanopiperidine (369 grams, 3 moles), and xylene (400 ml) were charged to a 3-liter flask and heated to reflux under nitrogen. The reflux temperature was slowly increased to 190° C. with a total of 50 grams of water removed. The solvent was removed at reduced pressure and the residue was filtered. The product obtained (1523 grams) was 6.71 by weight nitrogen.

EXAMPLE II

A substituted succinic anhydride (789 grams, 0.67 moles), 4-imino-3-cyanopiperdine (82.4 grams, 0.67 moles), mineral oil (580 grams) and toluene (600 grams) were charged to a 3-liter flask and heated to reflux under nitrogen. The reflux temperature was slowly increased to 180° C. with a total of 11 grams of water removed. The solvent was removed at reduced pressure and the residue was filtered. The product obtained (1415 grams) was 1.87% by weight nitrogen.

EXAMPLE III

An alkyl phenol (1236 grams, 1 mole), paraformaldehyde (30 grams, 1 mole), and 4-imino-3-cyanopiperidine (123 grams, 1 mole) were charged to a 3-liter flask and heated to reflux under nitrogen. The temperature was slowly increased to 155° C. with a total of 17.3 grams of water removed. The solvent was removed at reduced pressure. Mineral oil (914 grams) was added and the material was filtered. The product obtained (2125 grams) was 1.37% by weight nitrogen.

EXAMPLE IV

Dodecylamine (185 grams, 1 mole) and a solution of 11 grams of potassium hydroxide in 60 grams of water were charged to a 1-liter flask and warmed to 75° C. Acrylonitrile (53 grams, 1 mole) was added dropwise at 75°–85° C. The material was held at 75°–80° C. for 8 hours and the aqueous layer removed. A 37% aqueous solution of formaldehyde (81 grams, 1 mole) was added slowly to a solution of sodium bisulfite (104 grams, 1 mole) in 193 grams of water. The dodecylamine-acrylonitrile adduct was added dropwise to the sodium bisulfite-formaldehyde solution. A solution of potassium cyanide (65 grams, 1 mole) in 150 ml of water was added slowly at 55°–60° C., warmed to 80° C. and held at 80° C. for 2 hours. The waxy, organic layer was diluted with toluene, water washed, stripped at reduced pressure and filtered. The residue was added over one-half hour at 45°–50° C. under nitrogen to a solution of 11.2 grams of potassium t-butoxide in 700 grams of t-butyl alcohol. The solution was heated to 80° C. and held for 24 hours. The solvent was removed at reduced pressure and the residue was filtered. The product obtained (229 grams) was 12.78% by weight nitrogen.

EXAMPLE V

Octadecylamine (278 grams, 1 mole) and 200 ml of methanol were charged to a 1-liter flask and warmed to 55° C. Acrylonitrile (132.5 grams, 2.5 moles) was added dropwise over 2.5 hours. The solution was heated to reflux and held 6 hours. The solvent was removed at reduced pressure. The residue was diluted with 100 ml of t-butyl alcohol and added dropwise under nitrogen at 40°–50° C. to a solution of 11.2 grams of potassium t-butoxide in 600 ml of t-butyl alcohol. The solution was heated to 80° C. and held for 24 hours. The catalyst was neutralized with acetic acid, the solvent was removed at reduced pressure, and the residue was filtered. The product obtained (369 grams) was 9.14% by weight nitrogen.

EXAMPLE VI

The product from Example V (288 grams, 0.75 moles), isopropanol (750 ml), and triethylamine (75 ml) were charged to a 2-liter flask and warmed to 70° C. Hydrogen sulfide was bubbled through the solution at 0.2 moles per hour for 20 hours. The solvent was removed at reduced pressure and the residue was filtered. The product obtained (287 grams) was 7.07% by weight sulfur and 6.88% by weight nitrogen.

The compositions according to the present invention, which specific species have been illustrated in the above Examples I-VI, are versatile additives for lubricant and fuel compositions. The compositions of the present invention have been found to be useful additives for imparting friction modification as well as enhancing fuel economy and dispersancy properties of various lubricant and fuel compositions.

The composition of the present invention may be formulated with a particular functional fluid by the direct blending of the composition to the particular functional fluid, e.g., lubricating oil, or it may be formulated with the functional fluid in the form of a concentrate. Such a concentrate may be prepared by adding 1% to about 99% by weight of the composition or additive of the present invention to a substantially inert, normally liquid organic diluent or solvent such as benzene, toluene, xylene, petroleum naphtha, mineral oil, ethyleneglycol monomethyl ether or the like.

The compositions of the present invention formulated with the particular functional fluid or as a concentrate may contain other additives and chemistries such as dispersants, detergents, antioxidants, and the like. Such other additives and chemistries include, for example, detergents and dispersants of the ash-producing or ashless type, corrosion- and oxidation-inhibiting agents, pour point depressing agents, extreme pressure agents, color stabilizers and anti-foam agents. These other additives and chemistries are fully described and disclosed in U.S. Pat. No. 3,541,014; U.S. Pat. No. 4,289,635; and U.S. Pat. No. 4,266,945 which disclosures of these patents relating to such other additives and chemistries are hereby incorporated by reference for such disclosures.

It has previously been pointed out that the fuel consumption of engines lubricated with compositions containing the heterocyclic additives of the present invention may be decreased compared with that of engines lubricated with previously known lubricants. The improvement in fuel economy can be shown by the Pinto Friction Horsepower Test, in which a Ford Pinto engine is driven by a dynamometer at constant temperature as engine RPM and torque are measured by a digital tachometer and a precision dial manometer, respectively. Friction horsepower, as calculated from these values, is roughly proportional to fuel consumed and thus, decreases with improved fuel economy.

More specifically, the Ford Pinto FHP is a non-fired engine test, where a 4-cylinder Pinto engine is motored from between 400 and about 2800 RPM with a dynamometer and the amount of torque required (ft./lbs.) is measured. Measured torque is converted to frictional horsepower using the equation:

$$\text{Frictional Horsepower} = \frac{T \times N}{5252}$$

where
T=torque in ft./lbs.
N=engine speed in RPMs
5252=the equation constant.

FHP values of greater than 2.0% improvement are generally considered significant values, independent of the base line additive package.

Table I below lists the FHP values obtained for various, typical lubricating oils containing the heterocyclic additives of the present invention which were tested in the above described Ford Pinto friction horsepower test. It is again pointed out that the following results are provided for illustrative purposes only and are not to place any limitation on the scope of the invention where such scope is set out only in the claims. All parts and percentages are by weight.

TABLE I

| Fully Formulated Lubricant Oil Containing Product of Ex. No. | FHP Value (% Improvements) |
|---|---|
| 1% of product of Example I | 9.45 |
| 0.5% of product of Example IV | 2.3 |
| 1.0% of Product of Example V | 5.9 |

While the invention has been described and illustrated with reference to certain preferred embodiments thereof, those skilled in the art will appreciate that various changes, modifications and substitutions can be made therein without departing from the spirit of the invention. For example, different ratios of the different reactants to prepare the additive compounds of the present invention may be employed, other than preferred ranges set out hereinabove, also, the effective amount of the particular additive formulated with the lubricant oil may vary other than the amounts set out hereinabove, may be applicable as a consequence of the variations in the particular base stock of the oil or fuel or due to the type of engine in which it is used. It is intended, therefore, that the invention be limited only by the scope of the claims which follow:

What is claimed is:

1. An additive for functional fluids prepared by the process of reacting:

(I) at least one reactant of the formula:

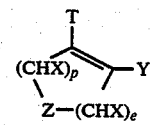

wherein Z is S, NR',

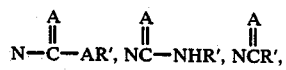

PR' or PR'A where A is O or S and R' is H, alkyl or alkenyl; p is 0 to 2; e is 0 to 2 wherein e+p is 2 to about 4; X is independently H, COOH, NH$_2$, $CONH_2$, $NHNH_2$, $OR'$, $COR'$, $NHR'$, $OH$, $SH$ or $CN$, where $R'$ is the same as defined above; wherein T is $NH_2$, $NHR'$ where $R'$ is the same as defined hereinabove, SH, OH or their tautomers; and Y is CN, $CO_2H$,

or $CH_2NH_2$ wherein A is the same as defined hereinabove; with (II) at least one reactant selected from the group consisting of hydrocarbyl substituted carboxylic acid or derivatives thereof, hydrocarbyl phenolic reactant, or mixtures thereof; wherein the reactants are heated to a temperature of from about 80° C. to the decomposition temperature of the mixture to effect acylation or condensation reaction, and wherein from about 0.25 to about 2.0 equivalents of reactant (I) is reacted with each equivalent of the hydrocarbyl carboxylic acid or derivative thereof and/or hydrocarbyl phenolic reactant.

2. The additive according to claim 1, wherein the reaction is effected by heating the reactants (I) and (II) to a temperature sufficient to effect reaction and wherein the water formed by said heating is removed.

3. The additive according to claim 1, wherein said hydrocarbyl carboxylic acid is at least 1 substituted succinic acid or derivative thereof consisting of substituent groups and succinic groups wherein the substituent groups are derived from polyalkylene, said polyalkylene being characterized by a Mn value of 100 to about 10,000 and a Mw/Mn value of 1.0 to about 4.0.

4. The additive according to claim 3, wherein said substituent group contains from about 8 to about 200 carbon atoms.

5. The additive according to claim 1, wherein X of compound (I) is H, Z is NR, T is $NH_2$, e is 1 and p is 2.

6. The additive according to claim 1, wherein X of the compound of (I) is H, Y is selected from $NH_2$ and $CONH_2$, Z is NR, T is $NH_2$, e is 1 and p is 2.

7. The additive according to claim 1, wherein X of the compound of (I) is H, Y of compound (I) is CN, Z is NR, T is $NH_2$, e is 1 and p is 2.

8. The additive according to claim 1, wherein the reactant (II) is a hydrocarbyl carboxylic acid and is heated with (I) to a temperature of from about 80° C. to the decomposition temperature of the mixture to effect acylation.

9. The additive according to claim 8, wherein said heating is at a temperature of from about 120° C. to about 175° C. to effect acylation.

10. The additive according to claim 1, wherein about 0.25 to about 2.0 equivalents of the compound of (I) are reacted with each equivalent of the hydrocarbyl carboxylic acid or derivative thereof of (II).

11. The additive according to claim 10, wherein about 0.4 to about 0.8 equivalents of the compound (I) are reacted with each equivalent of the hydrocarbyl carboxylic acid or derivatives thereof (II).

12. A concentrate for formulating functional fluids comprising a normally liquid, substantially inert organic solvent/diluent and from about 1% to about 99% by weight of the additive of claim 1.

13. A concentrate for formulating a functional fluid comprising a normally liquid, substantially inert organic solvent/diluent and from about 1% to about 99% by weight of the additive of claim 7.

14. A lubricating composition comprising a major amount of an oil of lubricating viscosity and a minor amount of at least one additive as defined in claim 1.

15. A lubricating composition comprising a major amount of an oil of lubricating viscosity and a minor amount of at least one additive as defined in claim 7.

16. A fuel composition comprising a major amount of the fuel and a minor amount of at least one additive as defined in claim 1.

17. A fuel composition comprising a major amount of the fuel and a minor amount of at least one additive as defined in claim 7.

* * * * *